(12) United States Patent
Kawamura

(10) Patent No.: US 10,888,295 B2
(45) Date of Patent: Jan. 12, 2021

(54) IMAGE PROCESSING APPARATUS, CONTROL DEVICE, IMAGE PROCESSING METHOD, AND IMAGE PROCESSING PROGRAM

(71) Applicant: FUJIFILM CORPORATION, Tokyo (JP)

(72) Inventor: Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 72 days.

(21) Appl. No.: 16/109,764

(22) Filed: Aug. 23, 2018

(65) Prior Publication Data
US 2019/0090837 A1 Mar. 28, 2019

(30) Foreign Application Priority Data

Sep. 28, 2017 (JP) ................................. 2017-187891

(51) Int. Cl.
*A61B 6/00* (2006.01)

(52) U.S. Cl.
CPC .............. *A61B 6/5282* (2013.01); *A61B 6/46* (2013.01); *A61B 6/488* (2013.01); *A61B 6/544* (2013.01)

(58) Field of Classification Search
CPC ......... A61B 6/5282; A61B 6/46; A61B 6/544; A61B 6/488
See application file for complete search history.

(56) References Cited

U.S. PATENT DOCUMENTS

| 9,140,803 B2 * | 9/2015 | Bertram | .................. A61B 6/032 |
| 2013/0121464 A1 * | 5/2013 | Tajima | .................... A61B 6/542 378/62 |
| 2015/0078528 A1 * | 3/2015 | Okada | ..................... G01T 1/026 378/97 |

(Continued)

FOREIGN PATENT DOCUMENTS

| JP | H08-66389 A | 3/1996 |
| JP | 2011-152154 A | 8/2011 |

(Continued)

OTHER PUBLICATIONS

Honda, JPH086389(A), "X-Ray Diagnostic Device", machine translated version, pp. 1-25. (Year: 1996).*

(Continued)

*Primary Examiner* — Yon J Couso
(74) *Attorney, Agent, or Firm* — Solaris Intellectual Property Group, PLLC

(57) ABSTRACT

A control unit of a console functions as an acquisition unit that acquires a radiographic image and imaging conditions in which the radiographic image has been captured. In addition, the control unit functions as a derivation unit that derives the amount of signal included in the radiographic image on the basis of a primary radiation distribution of the radiographic image derived on the basis of the imaging conditions or on the basis of the imaging conditions and a body thickness distribution of an object in the radiographic image and outputs the ratio of the derived amount of signal to the amount of noise included in the radiographic image as an index value of the amount of radiation emitted in the capture of the radiographic image.

12 Claims, 8 Drawing Sheets

(56) References Cited

U.S. PATENT DOCUMENTS

2017/0065244 A1    3/2017   Taki

FOREIGN PATENT DOCUMENTS

JP    2013-013789 A    1/2013
JP    2017-051395 A    3/2017

OTHER PUBLICATIONS

English language translation of the following: Office action dated Aug. 25, 2020 from the JPO in a Japanese patent application No. 2017-187891 corresponding to the instant patent application. This office action translation is submitted now in order to supplement the understanding of the cited references which are being disclosed in the instant Information Disclosure Statement.

* cited by examiner

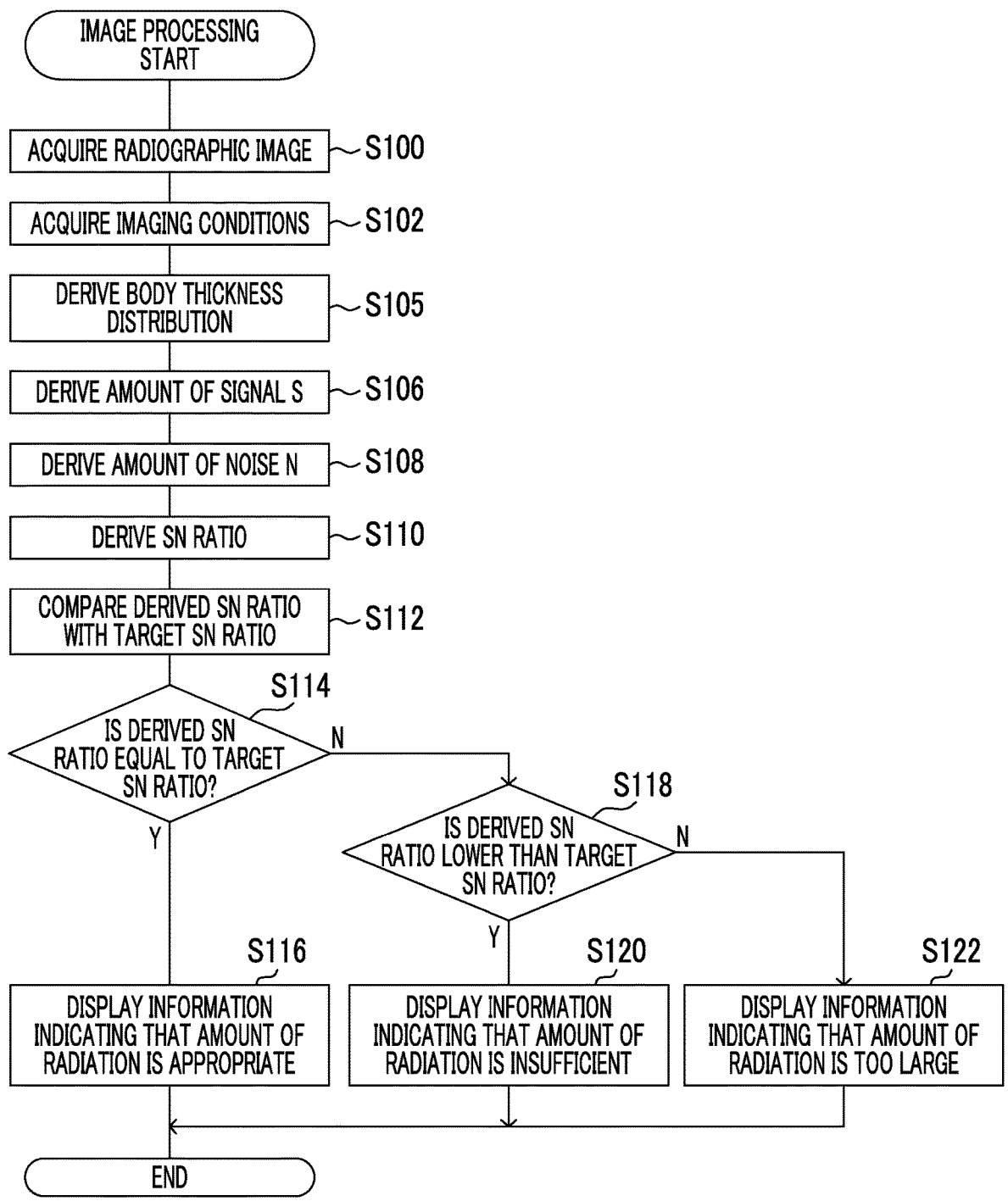

IMAGE PROCESSING APPARATUS, CONTROL DEVICE, IMAGE PROCESSING METHOD, AND IMAGE PROCESSING PROGRAM

CROSS REFERENCE TO RELATED APPLICATIONS

The present application claims priority under 35 U.S.C. § 119 to Japanese Patent Application No. 2017-187891 filed on Sep. 28, 2017. The above application is hereby expressly incorporated by reference, in its entirety, into the present application.

BACKGROUND

Field of the Invention

The present disclosure relates to an image processing apparatus, a control device, an image processing method, and an image processing program.

Related Art

In the related art, in the capture of a radiographic image, imaging is managed using the amount of radiation that reaches a radiation detector as an index. However, the number of scattered radiation components included in the radiation that reaches the radiation detector varies greatly depending on conditions, such as the body thickness of an object, whether or not a grid for removing scattered radiation is present, and the characteristics of the grid in a case in which the grid is used. As a result, in some cases, the amount of radiation is insufficient due to the influence of the scattered radiation and the captured radiographic image does not have desired image quality.

Furthermore, in the related art, in the capture of a radiographic image, since the improvement of the quality of a captured radiographic image is contrary to a reduction in the amount of radiation emitted to the object, it is preferable to capture a radiographic image with the minimum amount of radiation for obtaining image quality required for diagnosis. JP1996-66389A (JP-H08-66389A) discloses a technique which sets the SN ratio of a radiographic image and selects imaging conditions, such as a tube voltage, a tube current, and a radiation emission time, in which an object is irradiated with the minimum amount of radiation according to the set SN ratio.

In the technique disclosed in JP1996-66389A (JP-H08-66389A), as described above, the imaging conditions are selected according to the set SN ratio. However, imaging is not sufficiently managed and the radiographic image captured under the selected imaging conditions is unlikely to have the set SN ratio.

SUMMARY

The present disclosure has been made in view of the above-mentioned problems and an object of the present disclosure is to provide an image processing apparatus, a control device, an image processing method, and an image processing program that can further improve the quality of a radiographic image while preventing the management of the capture of the radiographic image from being complicated.

In order to achieve the object, according to the present disclosure, there is provided an image processing apparatus comprising: an acquisition unit that acquires a radiographic image and imaging conditions in which the radiographic image has been captured; and a derivation unit that derives an amount of signal included in the radiographic image on the basis of a primary radiation distribution of the radiographic image derived on the basis of the imaging conditions or on the basis of the imaging conditions and a body thickness distribution of an object in the radiographic image and outputs a ratio of the derived amount of signal to an amount of noise included in the radiographic image as an index value of an amount of radiation emitted in the capture of the radiographic image.

The image processing apparatus according to the present disclosure may further comprise a determination unit that determines whether the amount of radiation emitted in the capture of the radiographic image is excessive or insufficient on the basis of the index value and a predetermined target value and outputs a determination result.

In the image processing apparatus according to the present disclosure, in a case in which the index value is less than the target value, the determination unit may determine that the amount of radiation emitted in the capture of the radiographic image is less than a desired amount of radiation.

In the image processing apparatus according to the present disclosure, in a case in which the index value is greater than the target value, the determination unit may determine that the amount of radiation emitted in the capture of the radiographic image is more than the desired amount of radiation.

In the image processing apparatus according to the present disclosure, the derivation unit may output information indicating a warning in a case in which the index value is less than a predetermined target value and in a case in which the index value is greater than the predetermined target value.

In the image processing apparatus according to the present disclosure, the imaging conditions may include the amount of radiation emitted in the capture of the radiographic image. The image processing apparatus may further comprise a radiation amount derivation unit that derives the amount of radiation to be emitted, on the basis of the amount of radiation included in the imaging conditions, the index value, and a predetermined target value.

In the image processing apparatus according to the present disclosure, the acquisition unit may acquire a radiographic image captured by a pre-imaging operation which is performed before a main imaging operation and emits a smaller amount of radiation than the main imaging operation. The radiation amount derivation unit may derive the amount of radiation to be emitted in the main imaging operation.

In the image processing apparatus according to the present disclosure, the acquisition unit may acquire a radiographic image included in a series of radiographic images at a predetermined time during an imaging operation of capturing the series of radiographic images as a motion picture. The image processing apparatus may further comprise a control unit that performs control such that the emission of the radiation is stopped in the imaging operation in a case in which the index value is equal to or greater than a predetermined target value.

In order to achieve the object, according to the present disclosure, there is provided a control device comprising: an acquisition unit that acquires a radiographic image captured by a pre-imaging operation which is performed before a main imaging operation and emits a smaller amount of radiation than the main imaging operation and imaging conditions including an amount of radiation emitted in the capture of the radiographic image; a derivation unit that derives an amount of signal included in the radiographic image on the basis of a primary radiation distribution of the radiographic image derived on the basis of the imaging conditions or on the basis of the imaging conditions and a body thickness distribution of an object in the radiographic image and outputs a ratio of the derived amount of signal to an amount of noise included in the radiographic image as an index value of the amount of radiation emitted in the capture of the radiographic image; and a radiation amount derivation unit that derives the amount of radiation to be emitted in the main imaging operation, on the basis of the amount of radiation included in the imaging conditions, the index value, and a predetermined target value.

In order to achieve the object, according to the present disclosure, there is provided a control device comprising: an acquisition unit that acquires a radiographic image included in a series of radiographic images at a predetermined time during an imaging operation of capturing the series of radiographic images as a motion picture and imaging conditions in which the radiographic image has been captured; a derivation unit that derives an amount of signal included in the radiographic image on the basis of a primary radiation distribution of the radiographic image derived on the basis of the imaging conditions or on the basis of the imaging conditions and a body thickness distribution of an object in the radiographic image and outputs a ratio of the derived amount of signal to an amount of noise included in the radiographic image as an index value of the amount of radiation emitted in the capture of the radiographic image; and a control unit that performs control such that the emission of the radiation is stopped in the imaging operation in a case in which the index value is equal to or greater than a predetermined target value.

In order to achieve the object, according to the present disclosure, there is provided an image processing method comprising: acquiring a radiographic image and imaging conditions in which the radiographic image has been captured; deriving an amount of signal included in the radiographic image on the basis of a primary radiation distribution of the radiographic image derived on the basis of the imaging conditions or on the basis of the imaging conditions and a body thickness distribution of an object in the radiographic image; and outputting a ratio of the derived amount of signal to an amount of noise included in the radiographic image as an index value of an amount of radiation emitted in the capture of the radiographic image.

In order to achieve the object, according to the present disclosure, there is provided an image processing program that causes a computer to perform: acquiring a radiographic image and imaging conditions in which the radiographic image has been captured; deriving an amount of signal included in the radiographic image on the basis of a primary radiation distribution of the radiographic image derived on the basis of the imaging conditions or on the basis of the imaging conditions and a body thickness distribution of an object in the radiographic image; and outputting a ratio of the derived amount of signal to an amount of noise included in the radiographic image as an index value of an amount of radiation emitted in the capture of the radiographic image.

According to the present disclosure, it is possible to further improve the quality of a radiographic image while preventing the management of the capture of the radiographic image from being complicated.

BRIEF DESCRIPTION OF THE DRAWINGS

FIG. 9 is a flowchart illustrating another example of the flow of the image processing performed by the control unit of the console according to the first embodiment.

DETAILED DESCRIPTION

Hereinafter, embodiments of the present disclosure will be described in detail with reference to the drawings.

First Embodiment

Figure 1:
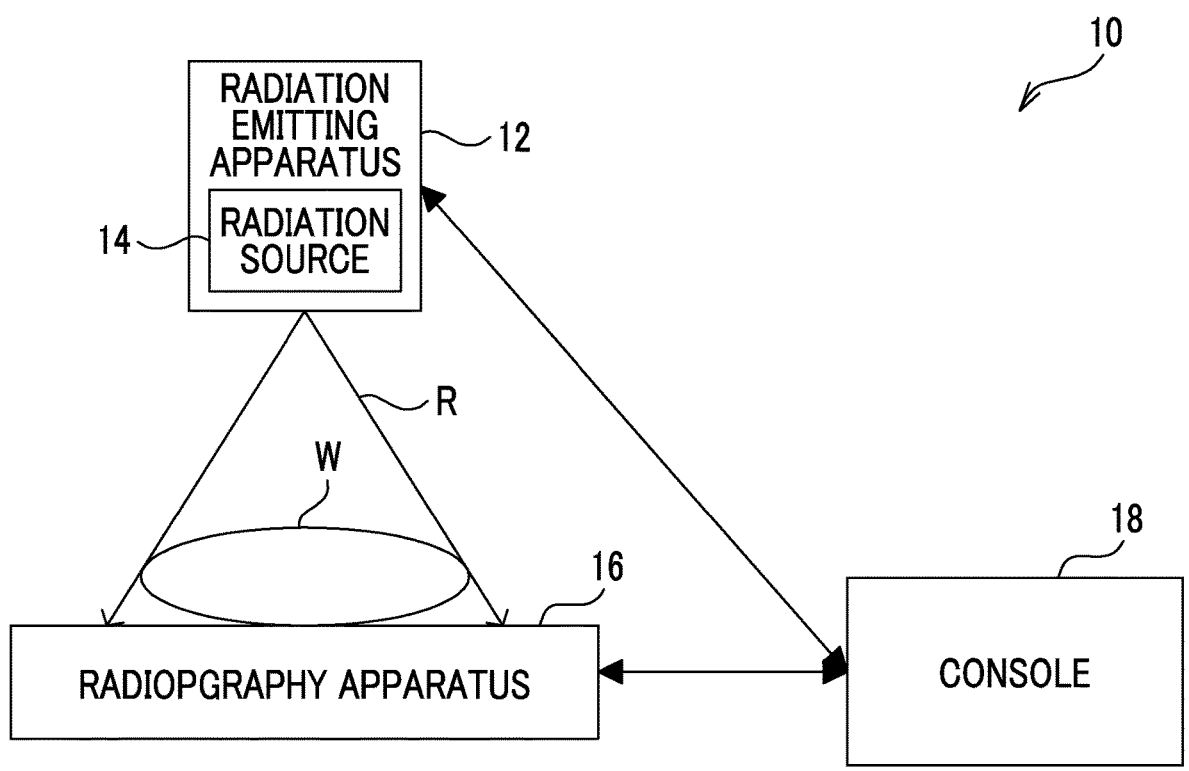
FIG. 1 is a configuration diagram illustrating an example of the configuration of a radiography system according to each embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. The console 18 according to this embodiment is an example of an image processing apparatus according to the present disclosure.

The radiation emitting apparatus 12 according to this embodiment includes a radiation source 14 that irradiates an object W, which is an example of an imaging target, with radiation R such as X-rays. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

The radiation emitting apparatus 12 includes a tube (not illustrated). In a case in which a command to emit the radiation R is received, the radiation emitting apparatus 12 emits the radiation R from the radiation source 14 according to set imaging conditions, such as a tube voltage, a tube current, and an irradiation period.

Figure 2:
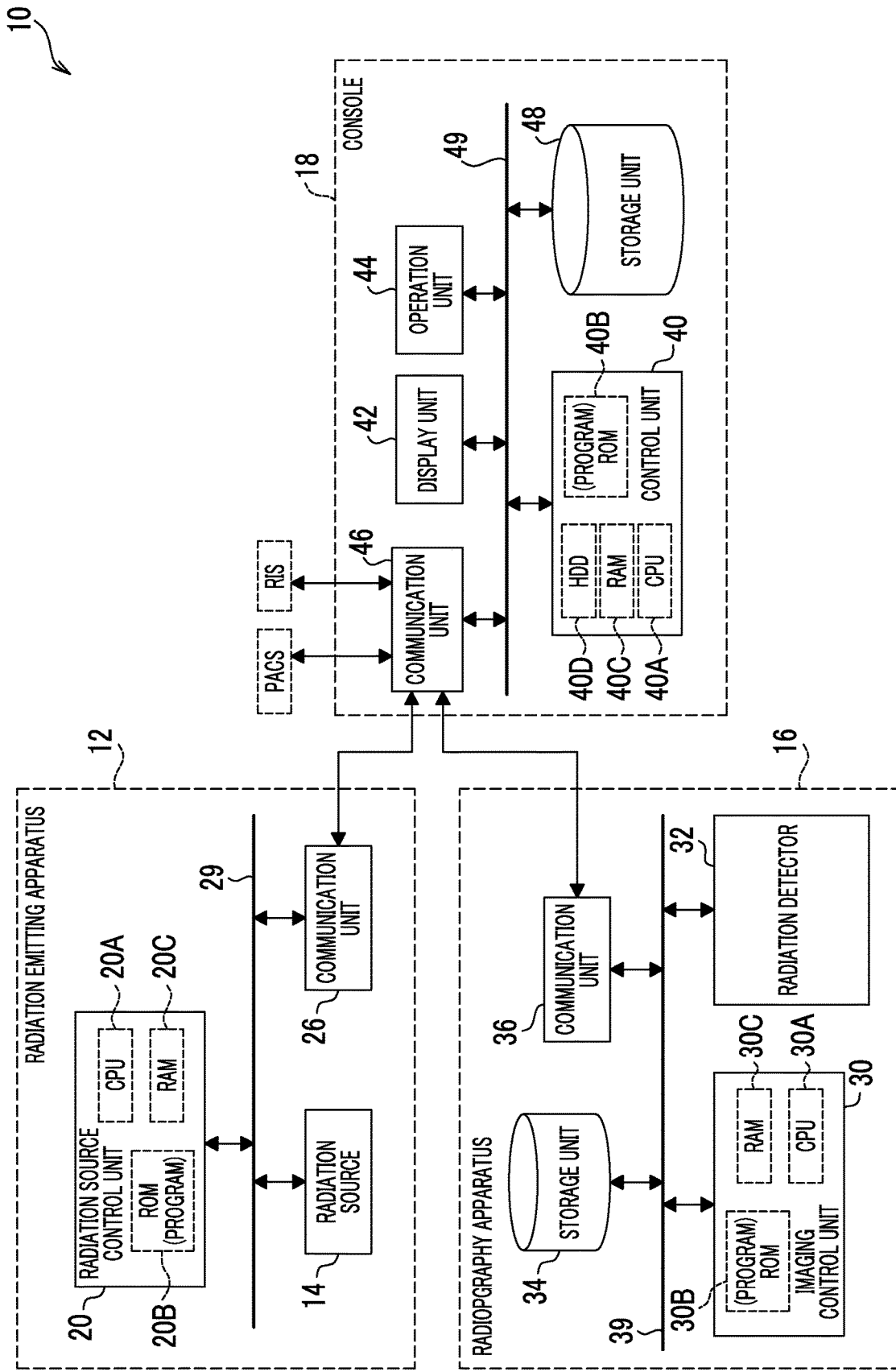
FIG. 2 is a block diagram illustrating an example of the configuration of a radiation emitting apparatus, a radiography apparatus, and a console according to each embodiment.

Next, the configuration of the radiation emitting apparatus 12, the radiography apparatus 16, and the console 18 according to this embodiment will be described with reference to FIG. 2. FIG. 2 is a block diagram illustrating an example of the configuration of the radiation emitting apparatus 12, the radiography apparatus 16, and the console 18 according to this embodiment.

The radiography apparatus 16 according to this embodiment is not particularly limited as long as it has a function of capturing a radiographic image corresponding to the radiation R transmitted through an object W and includes an imaging control unit 30, a radiation detector 32, a storage unit 34, and a communication unit 36. For example, the imaging control unit 30, the radiation detector 32, the storage unit 34, and the communication unit 36 are connected to each other through a bus 39 such as a system bus or a control bus.

The radiation detector 32 detects the radiation R transmitted through the object W under the control of the imaging control unit 30. The radiation detector 32 according to this embodiment is not particularly limited and may be, for example, an indirect-conversion-type radiation detector that converts the radiation R into light and converts the converted light into charge or a direct-conversion-type radiation detector that directly converts the radiation R into charge.

The imaging control unit 30 includes a central processing unit (CPU) 30A, a read only memory (ROM) 30B, and a random access memory (RAM) 30C. The CPU 30A controls the overall operation of the radiography apparatus 16. For example, various programs executed by the CPU 30A are stored in the ROM 30B in advance. The RAM 30C temporarily stores various types of data.

The storage unit 34 stores, for example, image data indicating captured radiographic images. An example of the storage unit 34 is a solid state drive (SSD). The storage unit 34 may be a device that is detachably provided in the radiography apparatus 16, such as a universal serial bus (USB) memory or a Secure Digital (SD) memory card (registered trademark).

The communication unit 36 transmits and receives various kinds of information to and from the console 18 using at least one of wireless communication or wired communication.

As illustrated in FIG. 2, the console 18 according to this embodiment includes a control unit 40, a display unit 42, an operation unit 44, a communication unit 46, and a storage unit 48. The control unit 40, the display unit 42, the operation unit 44, the communication unit 46, and the storage unit 48 are connected to each other through a bus 49 such as a system bus or a control bus.

The control unit 40 includes a CPU 40A, a ROM 40B, a RAM 40C, and a hard disk drive (HDD). The CPU 40A controls the overall operation of the console 18. For example, various programs executed by the CPU 40A are stored in the ROM 40B in advance. The RAM 40C temporarily stores various types of data. The HDD 40D stores various types of data.

The display unit 42 displays, for example, information related to imaging and the captured radiographic image. The operation unit 44 is used by a user to input, for example, a command to capture a radiographic image and a command related to image processing for the captured radiographic image. For example, the operation unit 44 may have the form of a keyboard or the form of a touch panel integrated with the display unit 42.

The communication unit 46 transmits and receives various kinds of information to and from the radiation emitting apparatus 12 and the radiography apparatus 16, using at least one of wireless communication or wired communication. In addition, the communication unit 46 transmits and receives various kinds of information to and from external systems, such as a picture archiving and communication system (PACS) and a radiology information system (RIS), using at least one of wireless communication or wired communication.

The storage unit 48 stores image data indicating the radiographic image acquired from the radiography apparatus 16 and various other types of data. An example of the storage unit 48 is an HDD or an SSD.

As illustrated in FIG. 2, the radiation emitting apparatus 12 according to this embodiment includes the radiation source 14, a radiation source control unit 20, and a communication unit 26. The radiation source 14, the radiation source control unit 20, and the communication unit 26 are connected to each other through a bus 29 such as a system bus or a control bus.

The radiation source control unit 20 includes a CPU 20A, a ROM 20B, and a RAM 20C. The CPU 20A controls the overall operation of the radiation emitting apparatus 12. For example, various programs executed by the CPU 20A are stored in the ROM 20B in advance. The RAM 20C temporarily stores various types of data.

The communication unit 26 transmits and receives various kinds of information to and from the console 18, using at least one of wireless communication or wired communication.

Next, as the operation of the console 18 according to this embodiment, an image processing operation of the console 18 will be described.

Figure 3:
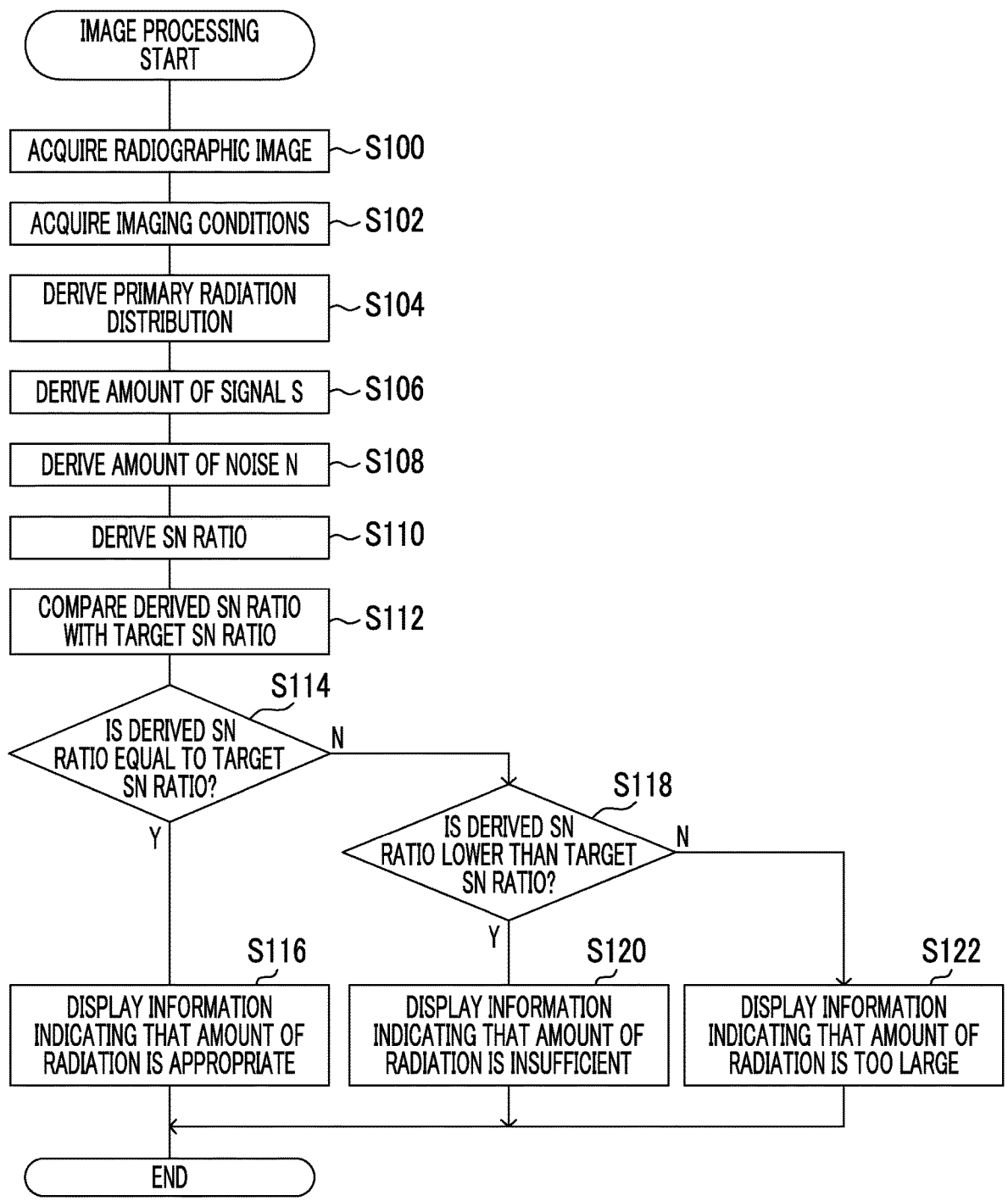
FIG. 3 is a flowchart illustrating an example of the flow of image processing performed by a control unit of a console according to a first embodiment.

FIG. 3 is a flowchart illustrating an example of the flow of image processing performed by the control unit 40 of the console 18 according to this embodiment. In the console 18 according to this embodiment, the control unit 40 executes an image processing program stored in the ROM 40B at a predetermined time to perform the image processing illustrated in FIG. 3. The predetermined time when the image processing is performed is not particularly limited. For example, the predetermined time is the time when the radiography apparatus 16 captures a radiographic image and the time when the user inputs a command to display a radiographic image through the operation unit 44. In addition, the CPU 40A of the control unit 40 according to this embodiment executes the image processing program such that the control unit 40 according to this embodiment functions as an example of an acquisition unit and a derivation unit according to the present disclosure.

In Step S100 of FIG. 3, the control unit 40 acquires a radiographic image obtained by imaging (hereinafter, simply referred to as a "radiographic image"). The acquisition destination of the radiographic image is not particularly limited as long as it is a device storing a desired radiographic image and may be, for example, any one of the storage unit 48 of the host apparatus, the radiography apparatus 16, and a PACS.

Then, in Step S102, the control unit 40 acquires the imaging conditions in which the radiographic image acquired in Step S100 has been captured. In this embodiment, the imaging conditions acquired in Step S102 include a tube voltage, a tube current, and a source-to-image distance (SID: a distance between a focus and an imaging surface of the radiation detector 32).

Then, in Step S104, the control unit 40 derives a primary radiation distribution of the radiographic image acquired in Step S100. The method used by the control unit 40 to derive the primary radiation distribution is not particularly limited. In this embodiment, for example, a primary radiation image and a scattered radiation image are calculated from a body thickness distribution T(x, y) of the object W in the acquired radiographic image on the basis of the following Expressions (1) and (2) to derive the primary radiation distribution.

$$Ip(x,y)=Io(x,y)\times \exp(-\mu \times T(x,y)) \quad (1)$$

$$Is(x,y)=Io(x,y)*S\sigma(T(x,y)) \quad (2)$$

In the above-mentioned Expressions (1) and (2), (x, y) is the coordinates of a pixel position of the radiographic image, Ip(x, y) is a primary radiation image at the pixel position (x, y), and Is(x, y) is a scattered radiation image at the pixel position (x, y). In addition, Io(x, y) is the amount of radiation incident on the surface of the object W at the pixel position (x, y), μ is a linear attenuation coefficient of the object, and Sσ(T(x, y)) is a convolution kernel indicating scattering characteristics corresponding to the body thickness of the object W at the pixel position (x, y). The above-mentioned Expression (1) is based on a known exponential attenuation rule and Expression (2) is based on the method described in J. M. Boon et al., "An analytical model of the scattered radiation distribution in diagnostic radiology, Med. Phys. 15(5), September/October 1988" (Reference Document 1). The amount of radiation Io(x, y) incident on the surface of the object W is canceled by division in a case in which a scattered radiation content distribution S(x, y) is calculated even if the amount of radiation Io(x, y) is defined as any value. Therefore, the amount of radiation Io(x, y) may be any value. For example, the amount of radiation Io(x, y) may be "1".

In addition, the body thickness distribution T(x, y) of the object W may be calculated by converting the pixel value of the radiographic image into a body thickness with a linear attenuation coefficient value, assuming that a luminance distribution in the radiographic image is substantially matched with the body thickness distribution of the object W. Alternatively, the body thickness of the object W may be measured by, for example, a sensor or may be approximated by a model such as a cube or an elliptical column.

In Expression (2), "*" is an operator indicating convolution calculation. The property of the kernel changes depending on, for example, the distribution of the irradiation field, the distribution of the composition of the object W, imaging conditions, and the characteristics of the radiation detector 32 in addition to the body thickness of the object W. According to the method described in Reference Document 1, scattered radiation can be approximated by the convolution of a point spread function (Sσ(T(x, y)) in Expression (2)) for primary radiation. In addition, Sσ(T(x, y)) can be experimentally calculated according to, for example, irradiation field information, object information, imaging conditions.

In addition, Sσ(T(x, y)) may be calculated on the basis of the irradiation field information, the object information, and the imaging conditions in imaging. Alternatively, a table in which various kinds of irradiation field information, various kinds of object information, and various imaging conditions are associated with Sσ(T(x, y)) may be stored in the storage unit 48 and Sσ(T(x, y)) may be calculated on the basis of the irradiation field information, the object information, and the imaging conditions in imaging with reference to the table stored in the storage unit 48. In addition, Sσ(T(x, y)) may be approximated by T(x, y).

Then, in Step S106, the control unit 40 derives the amount of signal S included in the radiographic image on the basis of the primary radiation distribution derived in Step S104. The method used by the control unit 40 to derive the amount of signal S is not particularly limited. For example, in this embodiment, the power spectrum of the primary radiation is derived as the amount of signal S and the amount of signal S is used as the total amount of signal in the radiographic image including various spatial frequency components.

In a case in which a primary radiation distribution at the coordinates (x, y) is p(x, y) and the Fourier spectrum of the primary radiation at a spatial frequency (u, v) is P(u, v), the power spectrum $P_p(u, v)$ of the primary radiation is derived by the following Expression (3).

$$P_p(u,v)=|P(u,v)|^2 \quad (3)$$

The control unit 40 may derive the amount of signal S limited to a spatial frequency of 1.0 (cyc/mm) that is important in the capture of a radiographic image.

Then, in Step S108, the control unit 40 derives the amount of noise N included in the radiographic image. The method used by the control unit 40 to derive the amount of noise N is not particularly limited. For example, in this embodiment, a power spectrum of noise is used to derive the amount of noise N as the total amount of noise in the radiographic image including various spatial frequency components.

Noise is a density difference caused by random granular components that are not related to the structure of the object W. The amount of radiation R (primary radiation and scattered radiation) that reaches the radiation detector 32 is generated as a noise component following the Poisson distribution and a power spectrum $P_u(u, v)$ of noise is proportional to the square root of the amount of radiation R which has reached the radiation detector 32. In a case in which the amount of signal S is derived, similarly, the control unit 40 may derive the amount of noise N limited to a spatial frequency of 1.0 (cyc/mm) that is important in the capture of a radiographic image.

Then, in Step S110, the control unit 40 derives the ratio of the amount of signal S derived in Step S106 to the amount of noise N to derive an SN ratio. Specifically, the control unit 40 derives the ratio of the power spectrum $P_p(u, v)$ of primary radiation to the power spectrum $P_u(u, v)$ of noise to derive the SN ratio for each spatial frequency. As in the case of the derivation of the amount of signal S and the amount of noise N, the control unit 40 may derive the SN ratio limited to a spatial frequency of 1.0 (cyc/mm) that is important in the capture of a radiographic image.

Then, in Step S112, the control unit 40 compares the SN ratio derived in Step S110 (hereinafter, referred to as a "derived SN ratio") with a target SN ratio. Here, the target SN ratio is the SN ratio of the radiographic image at which, for example, the quality of a radiographic image desired by the user and the quality of a radiographic image required for clinical testing are obtained. In this embodiment, the target SN ratio is obtained in advance and is stored in the console 18.

Then, in Step S114, the control unit 40 determines whether the derived SN ratio is equal to the target SN ratio on the basis of the comparison result obtained in Step S112. In a case in which the derived SN ratio is equal to the target SN ratio, the determination result in Step S114 is "Yes" and the process proceeds to Step S116. In this embodiment, in a case in which the derived SN ratio is included in a range including the target SN ratio and an error, the derived SN ratio is determined to be equal to the target SN ratio.

Figure 4:
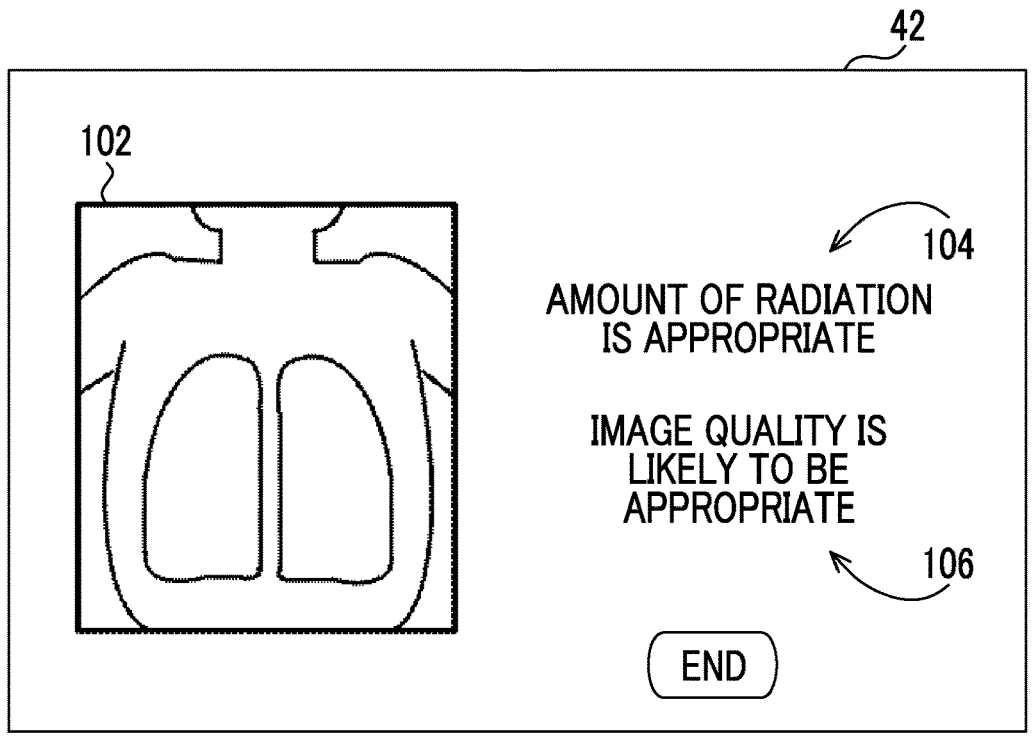
FIG. 4 is a diagram illustrating an example of a state in which information related to the amount of radiation is displayed on a display unit in a case in which the amount of radiation is appropriate in the first embodiment.

As such, in a case in which the derived SN ratio is equal to the target SN ratio, the amount of radiation R is appropriate. Therefore, in Step S116, the control unit 40 displays information indicating that the amount of radiation R emitted in the capture of a radiographic image is appropriate on the display unit 42 and ends the image processing. In this embodiment, for example, as illustrated in FIG. 4, the control unit 40 displays, on the display unit 42, information indicating that the captured radiographic image has appropriate (desired) image quality since the amount of radiation R is appropriate. FIG. 4 illustrates a state in which a radiographic image 102 acquired in Step S100, information 104 indicating that the amount of radiation is appropriate, and information 106 indicating that image quality is appropriate are displayed on the display unit 42.

On the other hand, in a case in which the derived SN ratio is not equal to the target SN ratio, the determination result in Step S114 is "No" and the process proceeds to Step S118. In Step S118, the control unit 40 determines whether the derived SN ratio is lower than the target SN ratio on the basis of the comparison result obtained in Step S112. In a case in which the derived SN ratio is lower than the target SN ratio, the determination result in Step S118 is "Yes" and the process proceeds to Step S120.

Figure 5:
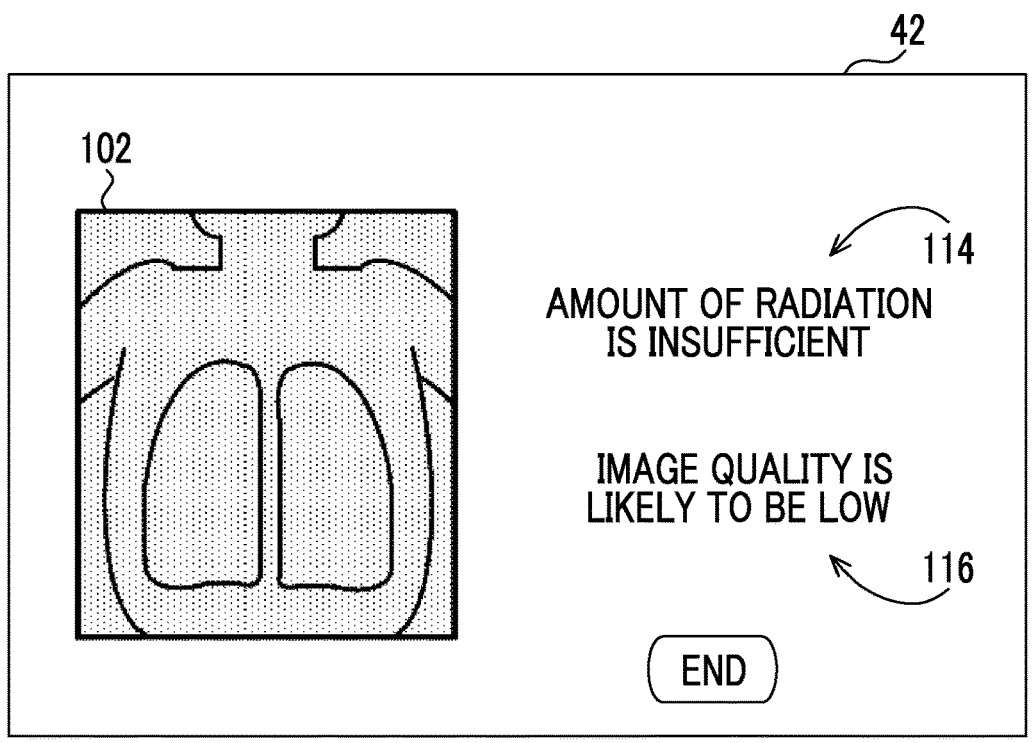
FIG. 5 is a diagram illustrating an example of a state in which information related to the amount of radiation is displayed on the display unit in a case in which the amount of radiation is insufficient in the first embodiment.

As such, in a case in which the derived SN ratio is lower than the target SN ratio, the amount of noise N increases since the amount of radiation R is insufficient. Therefore, in Step S120, the control unit 40 displays information indicating that the amount of radiation R emitted in the capture of a radiographic image is insufficient on the display unit 42 and ends the image processing. In addition, in this embodiment, for example, as illustrated in FIG. 5, the control unit 40 displays, on the display unit 42, information indicating that the captured radiographic image does not have appropriate (desired) image quality due to a reduction in granularity since the amount of radiation R is insufficient. FIG. 5 illustrates a state in which the radiographic image 102 acquired in Step S100, information 114 indicating that the amount of radiation is insufficient, and information 116 indicating that image quality is not appropriate are displayed on the display unit 42.

Figure 6:
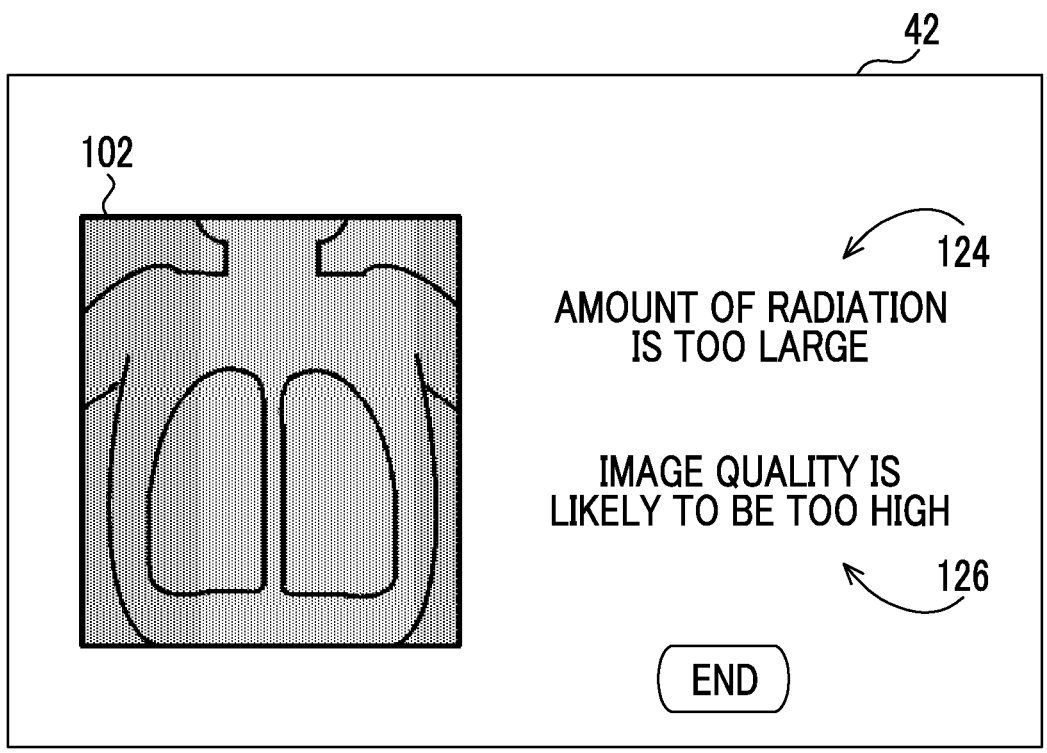
FIG. 6 is a diagram illustrating an example of a state in which information related to the amount of radiation is displayed on the display unit in a case in which the amount of radiation is too large in the first embodiment.

On the other hand, in a case in which the derived SN ratio is not lower than the target SN ratio, the determination result in Step S118 is "No" and the process proceeds to Step S122. In this case, the derived SN ratio may be higher than the target SN ratio. As such, in a case in which the derived SN ratio is higher than the target SN ratio, the amount of radiation R is too large and the amount of signal S increases. Therefore, in Step S122, the control unit 40 displays information indicating that the amount of radiation R emitted in the capture of a radiographic image is too large on the display unit 42 and ends the image processing. In this embodiment, for example, as illustrated in FIG. 6, the control unit 40 displays, on the display unit 42, information indicating that the captured radiographic image does not have appropriate (desired) image quality due to a reduction in contrast since the amount of radiation R is too large. FIG. 6 illustrates a state in which the radiographic image 102 acquired in Step S100, information 124 indicating that the amount of radiation is too large, and information 126 indicating that image quality is not appropriate are displayed on the display unit 42.

With the above-mentioned process, the console 18 according to this embodiment can determine whether the amount of radiation R emitted in imaging is excessive or insufficient, using the SN ratio of the captured radiographic image as an index. In a case in which the amount of radiation R is excessive or insufficient, it is possible to warn that the amount of radiation R is excessive or insufficient. In addition, the console 18 according to this embodiment can determine the quality of the radiographic image on the basis of the determination result of whether the amount of radiation R is excessive or insufficient. Therefore, according to the console 18 of this embodiment, it is possible to further improve the quality of a radiographic image while preventing the management of the capture of the radiographic image from being complicated.

Second Embodiment

In some cases, for example, before an imaging operation (hereinafter, referred to as a "main imaging operation") of capturing a radiographic image used for interpretation for the purpose of diagnosis, the positioning of a subject is checked by a radiographic image (hereinafter, referred to as a "pre-shot image") captured by an imaging operation (hereinafter, referred to as a "pre-imaging operation") of emitting a smaller amount of radiation R than that in the main imaging operation. In this embodiment, an aspect in which the amount of radiation in the main imaging operation is managed using the SN ratio of the pre-shot image obtained in the pre-imaging operation as an index will be described.

In this embodiment, the same configuration and operation as those described in the first embodiment are denoted by the same reference numerals and the detailed description thereof will not be repeated. In this embodiment, the console 18 is an example of a control device according to the present disclosure.

Since the configuration of a radiography system 10 according to this embodiment is the same as the configuration of the radiography system 10 (see FIGS. 1 and 2) according to the first embodiment, the description thereof will not be repeated. In this embodiment, a portion of image processing performed by the control unit 40 of the console 18 is different from that of the image processing (see FIG. 3) according to the first embodiment. Therefore, the image processing performed by the control unit 40 according to this embodiment will be described.

Figure 7:
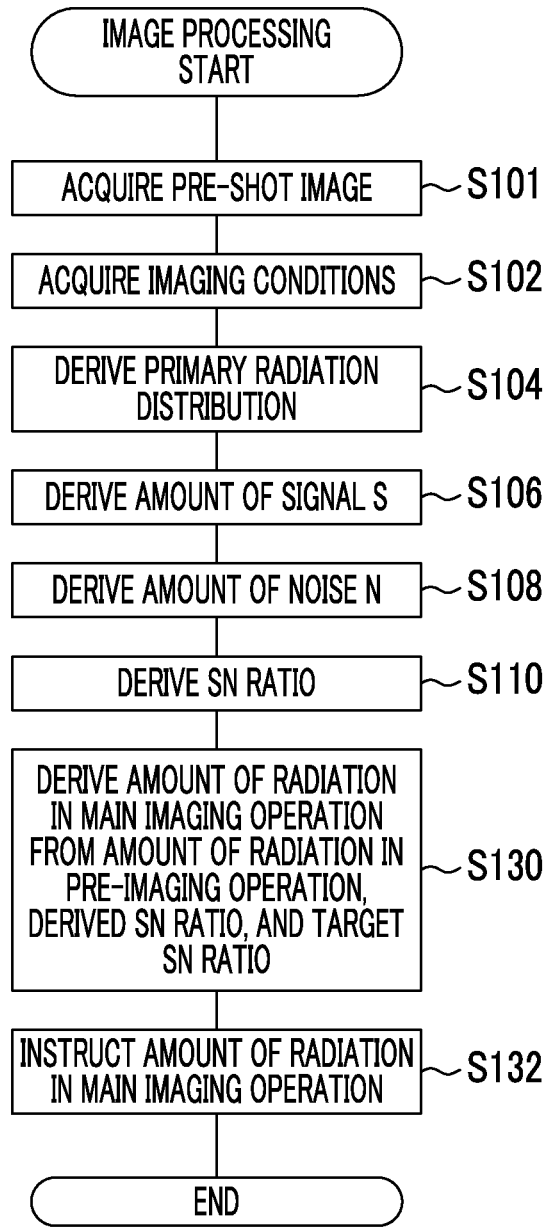
FIG. 7 is a flowchart illustrating an example of the flow of image processing performed by a control unit of a console according to a second embodiment.

FIG. 7 is a flowchart illustrating an example of the flow of the image processing performed by the control unit 40 according to this embodiment. As illustrated in FIG. 7, the image processing according to this embodiment differs from the image processing (see FIG. 3) according to the first embodiment in that Step S101 is performed instead of Step S100 and Steps S130 and S132 are performed instead of Steps S112 to S122.

In this embodiment, as illustrated in FIG. 7, first, in Step S101, the control unit 40 acquires a pre-shot image obtained by the pre-imaging operation. The control unit 40 derives the SN ratio of the pre-shot image acquired in Step S101 in Steps S104 to S110.

In Step S130, the control unit 40 derives the amount of radiation R to be emitted in the main imaging operation (hereinafter, simply referred to as a "main imaging dose") from the amount of radiation R emitted in the pre-imaging operation, the derived SN ratio, and the target SN ratio.

Specifically, in a case in which the amount of radiation R emitted in the pre-imaging operation is $X_0$, the main imaging dose is $X_1$, the derived SN ratio is $SNR_0$, and the target SN ratio is $SNR_1$, the main imaging dose $X_1$ is derived by the following Expression (4).

$$X_1 = X_0 \times (SNR_1^2 / SNR_0^2) \quad (4)$$

Then, in Step S132, the control unit 40 instructs the radiation emitting apparatus 12 of the main imaging dose derived in Step S130 and ends the image processing. In addition, the control unit 40 may not instruct the main imaging dose, but may instruct the radiation emitting apparatus 12 of the imaging conditions in which the derived main imaging dose is obtained.

With the above-mentioned process, the radiation emitting apparatus 12 according to this embodiment performs the main imaging operation with the amount of radiation instructed by the console 18, using the SN ratio of the pre-shot image as an index. Therefore, in the main imaging operation, a radiographic image with desired quality is captured. According to the console 18 of this embodiment, it is possible to further improve the quality of a radiographic image while preventing the management of the capture of a radiographic image from being complicated.

Third Embodiment

A technique has been known in which the console 18 manages the amount of radiation R emitted to an object during the capture of a radiographic image. In this embodiment, an aspect will be described in which the amount of radiation R emitted to the object is managed, using the SN ratio of an image selected from a plurality of still images forming a motion picture as an index, in a case in which the radiographic images of the object are captured as the motion picture.

In this embodiment, the same configuration and operation as those described in the first embodiment are denoted by the same reference numerals and the detailed description thereof will not be repeated. In this embodiment, the console 18 is an example of the control device according to the present disclosure.

Since the configuration of a radiography system 10 according to this embodiment is the same as the configuration of the radiography system 10 (see FIGS. 1 and 2) according to the first embodiment, the description thereof will not be repeated. In this embodiment, a portion of image processing performed by the control unit 40 of the console 18 is different from that of the image processing (see FIG. 3) according to the first embodiment. Therefore, the image processing performed by the control unit 40 according to this embodiment will be described.

Figure 8:
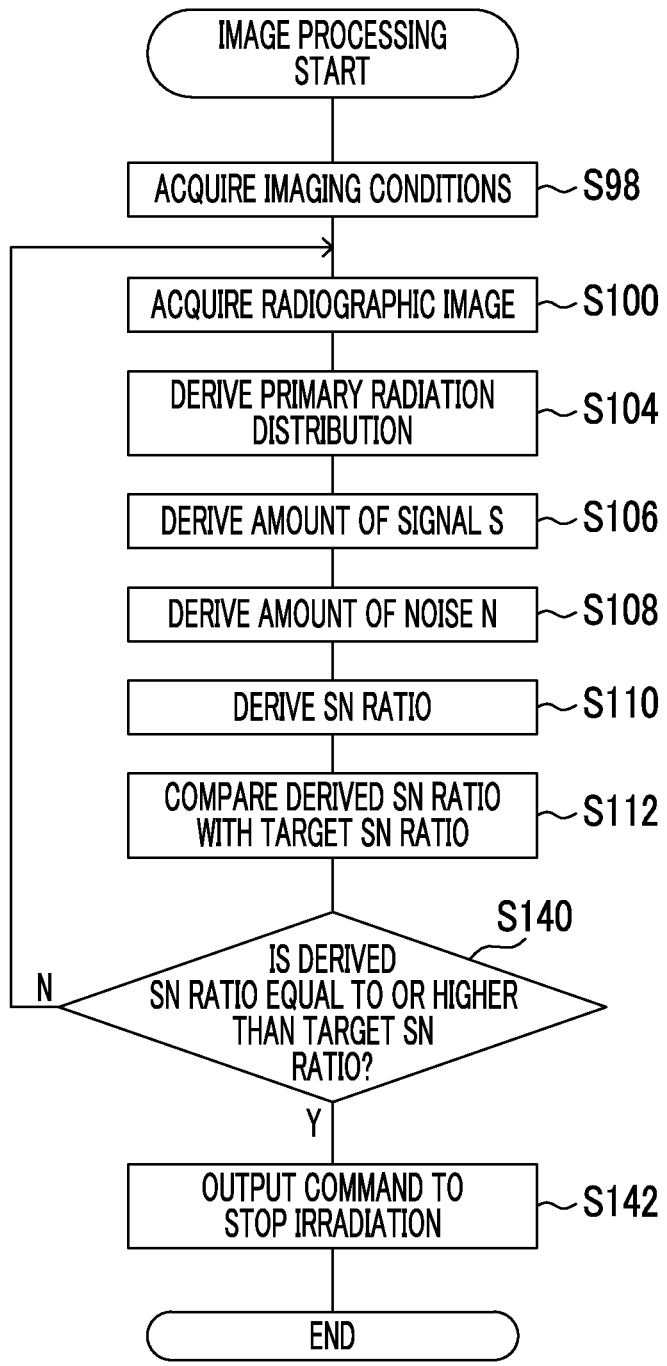
FIG. 8 is a flowchart illustrating an example of the flow of image processing performed by a control unit of a console according to a third embodiment.

FIG. 8 is a flowchart illustrating an example of the flow of the image processing performed by the control unit 40 according to this embodiment. In this embodiment, in a case in which a command to capture a motion picture is issued, the control unit 40 executes the image processing program stored in the ROM 40B to perform the image processing illustrated in FIG. 8.

As illustrated in FIG. 8, the image processing according to this embodiment differs from the image processing (see FIG. 3) according to the first embodiment in that Step S98 is performed before Step S100, Step S102 is not included, and Steps S140 and S142 are performed instead of Steps S114 to S122.

In this embodiment, as illustrated in FIG. 8, first, in Step S98, the control unit 40 acquires the imaging conditions for capturing a motion picture. The imaging conditions acquired in this step are the same as the imaging conditions acquired in Step S102 of the image processing according to each of the above-described embodiments.

In this embodiment, in Step S100, the control unit 40 acquires a radiographic image (still image) from the radiation detector 32 at a predetermined time during the capture of a motion picture and proceeds to Step S106. The predetermined time is not particularly limited. For example, the predetermined time may be determined according to a frame rate in the capture of a motion picture.

With the lapse of the emission time of the radiation R, the amount of signal S increases and the SN ratio increases. In this embodiment, in Step S140, the control unit 40 determines whether the derived SN ratio is equal to or higher than the target SN ratio (the derived SN ratio the target SN ratio). In a case in which the derived SN ratio is lower than the target SN ratio, the determination result in Step S140 is "No" and the process returns to Step S100 and each process in Steps S104 to S112 is repeated. On the other hand, in a case in which the derived SN ratio is equal to or higher than the target SN ratio, the determination result in Step S140 is "Yes" and the process proceeds to Step S142.

In Step S142, the control unit 40 outputs a command to stop the emission of the radiation R to the radiation emitting apparatus 12 and ends the image processing. The radiation emitting apparatus 12 stops the emission of the radiation R in response to the command input from the console 18.

With the above-mentioned process, the radiation emitting apparatus 12 according to this embodiment performs the main imaging operation with the instructed amount of radiation, using the SN ratio of the pre-shot image as an index. Therefore, in the main imaging operation, a radiographic image with desired quality is captured.

As such, the console 18 according to this embodiment manages the amount of radiation R emitted to the object, using the SN ratio of the captured radiographic image as an index, during the capture of a radiographic image. Therefore, it is possible to appropriately determine the time when the emission of the radiation R is stopped. As a result, according to the console 18 of this embodiment, it is possible to further improve the quality of a radiographic image while preventing the management of the capture of a radiographic image from being complicated.

In addition, in this embodiment, the aspect in which the console 18 manages the amount of radiation using the SN ratio of the still image forming the motion picture in the capture of a motion picture as an index has been described. However, the invention is not limited to this aspect. For example, the console 18 may manage the amount of radiation, using the SN ratio of a pixel for detecting the amount of radiation in the radiation detector 32 as an index, in the capture of a still image.

For example, the radiography apparatus 16 may determine at least one of the start of the emission of the radiation R or the stop of the emission of the radiation R, without being controlled by the console 18. In a case in which an imaging operation is performed using the radiation detector 32, the radiography apparatus 16 may perform the above-mentioned image processing (FIG. 8).

As described above, the control unit 40 of the console 18 according to each of the above-described embodiments functions as an acquisition unit that acquires a radiographic image and the imaging conditions in which the radiographic image has been captured. In addition, the control unit 40 functions as a derivation unit that derives the amount of signal S included in the radiographic image on the basis of the primary radiation distribution of the radiographic image derived on the basis of the imaging conditions or on the basis of the imaging conditions and the body thickness distribution of the object in the radiographic image and outputs the SN ratio which is the ratio of the derived amount of signal S to the amount of noise N included in the radiographic image as an index value of the amount of radiation R emitted in the capture of a radiographic image.

In general, the console (radiography system) according to the related art manages imaging, using the amount of radiation that reaches the radiation detector as an index, in the capture of a radiographic image. For example, in a case in which the amount of radiation that reaches the radiation detector is equal to or more than a predetermined amount of radiation, the console may stop the emission of the radiation to manage imaging.

However, the number of scattered radiation components included in the radiation that reaches the radiation detector varies greatly depending on conditions, such as the body thickness of the object, whether or not a grid for removing scattered radiation is present, and the characteristics of the grid in a case in which the grid is used. For example, as the body thickness of the object increases, the number of scattered radiation components increases. Therefore, in a case in which these conditions change, the number of scattered radiation components changes. The amount of radiation is excessive or insufficient due to the influence of the scattered radiation components. As a result, the captured radiographic image is likely to have desired image quality. In addition, in a case in which the above-mentioned conditions are managed in order to capture a radiographic image with desired image quality, the management is likely to impose a large burden on the operator since there are many types of conditions.

In contrast, according to the console 18 of each of the above-described embodiments, it is possible to manage the capture of a radiographic image, using the SN ratio which is the ratio of the amount of signal S to the amount of noise derived from the radiographic image as the index value of the amount of radiation R.

Therefore, according to the console 18 of each of the above-described embodiments, it is possible to further improve the quality of the radiographic image while preventing the management of the capture of the radiographic image from being complicated.

In each of the above-described embodiments, the aspect in which the amount of signal S in the radiographic image is derived on the basis of the primary radiation distribution of the radiographic image derived on the basis of the imaging conditions has been described. However, a method for deriving the amount of signal S is not particularly limited. For example, the amount of signal S may be derived on the basis of the imaging conditions and the body thickness distribution of the object (imaging part). In this case, for example, as in image processing illustrated in FIG. 9, Step S105 may be performed instead of Step S104 in the image processing (see FIG. 3) according to the first embodiment, the body thickness distribution of the object may be derived in Step S105, and the amount of signal S may be derived on the basis of the derived body thickness distribution and the imaging conditions in Step S106.

In each of the above-described embodiments, various processors other than the CPU 40A may perform the image processing performed by the execution of software (program) by the CPU 40A of the control unit 40 in the console 18. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which the image processing program is stored (installed) in the ROM 40B in advance has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, the image processing program may be downloaded from an external apparatus through the network.

What is claimed is:

1. An image processing apparatus comprising at least one processor, the processor configured to:
   acquire a radiographic image and imaging conditions in which the radiographic image has been captured; and
   derive an amount of signal included in the radiographic image on the basis of the imaging conditions and a body thickness distribution of an object in the radiographic image and outputs a ratio of the derived amount of signal to an amount of noise included in the radiographic image as an index value of an amount of radiation emitted in the capture of the radiographic image; wherein
   the imaging conditions include the amount of radiation emitted in the capture of the radiographic image, and the processor further configured to derive the amount of radiation to be emitted, on the basis of the amount of radiation included in the imaging conditions, the index value, and a predetermined target value;
   the processor acquires a radiographic image captured by a pre-imaging operation which is performed before a main imaging operation and emits a smaller amount of radiation than the main imaging operation, and
   the processor derives the amount of radiation to be emitted in the main imaging operation.

2. The image processing apparatus according to claim 1, the processor further configured to:
   determine whether the amount of radiation emitted in the capture of the radiographic image is excessive or insufficient on the basis of the index value and a predetermined target value and outputs a determination result.

3. The image processing apparatus according to claim 2, wherein, in a case in which the index value is less than the target value, the processor determines that the amount of radiation emitted in the capture of the radiographic image is less than a desired amount of radiation.

4. The image processing apparatus according to claim 2, wherein, in a case in which the index value is greater than the target value, the processor determines that the amount of radiation emitted in the capture of the radiographic image is more than the desired amount of radiation.

5. The image processing apparatus according to claim 1, wherein the processor outputs information indicating a warning in a case in which the index value is less than a predetermined target value and in a case in which the index value is greater than the predetermined target value.

6. A control device comprising at least one processor, the processor configured to:
acquire a radiographic image captured by a pre-imaging operation which is performed before a main imaging operation and emits a smaller amount of radiation than the main imaging operation and imaging conditions including an amount of radiation emitted in the capture of the radiographic image;
derive an amount of signal included in the radiographic image on the basis of a primary radiation distribution of the radiographic image derived on the basis of the imaging conditions or on the basis of the imaging conditions and a body thickness distribution of an object in the radiographic image and outputs a ratio of the derived amount of signal to an amount of noise included in the radiographic image as an index value of the amount of radiation emitted in the capture of the radiographic image; and
derive the amount of radiation to be emitted in the main imaging operation, on the basis of the amount of radiation included in the imaging conditions, the index value, and a predetermined target value.

7. A control device comprising at least one processor, the processor configured to:
acquire a radiographic image included in a series of radiographic images at a predetermined time during an imaging operation of capturing the series of radiographic images as a motion picture and imaging conditions in which the radiographic image has been captured;
derive an amount of signal included in the radiographic image on the basis of a primary radiation distribution of the radiographic image derived on the basis of the imaging conditions or on the basis of the imaging conditions and a body thickness distribution of an object in the radiographic image and outputs a ratio of the derived amount of signal to an amount of noise included in the radiographic image as an index value of the amount of radiation emitted in the capture of the radiographic image; and
perform control such that the emission of the radiation is stopped in the imaging operation in a case in which the index value is equal to or greater than a predetermined target value.

8. An image processing method comprising:
acquiring a radiographic image and imaging conditions in which the radiographic image has been captured, wherein the imaging conditions include the amount of radiation emitted in the capture of the radiographic image;
deriving an amount of signal included in the radiographic image on the basis of the imaging conditions and a body thickness distribution of an object in the radiographic image; and
outputting a ratio of the derived amount of signal to an amount of noise included in the radiographic image as an index value of an amount of radiation emitted in the capture of the radiographic image;
deriving the amount of radiation to be emitted, on the basis of the amount of radiation included in the imaging conditions, the index value, and a predetermined target value;
acquiring a radiographic image captured by a pre-imaging operation which is performed before a main imaging operation and emits a smaller amount of radiation than the main imaging operation; and
deriving the amount of radiation to be emitted in the main imaging operation.

9. A non-transitory computer-readable storage medium that stores an image processing program that causes a computer to perform:
acquiring a radiographic image and imaging conditions in which the radiographic image has been captured; wherein the imaging conditions include the amount of radiation emitted in the capture of the radiographic image;
deriving an amount of signal included in the radiographic image on the basis of the imaging conditions and a body thickness distribution of an object in the radiographic image; and
outputting a ratio of the derived amount of signal to an amount of noise included in the radiographic image as an index value of an amount of radiation emitted in the capture of the radiographic image;
deriving the amount of radiation to be emitted, on the basis of the amount of radiation included in the imaging conditions, the index value, and a predetermined target value;
acquiring a radiographic image captured by a pre-imaging operation which is performed before a main imaging operation and emits a smaller amount of radiation than the main imaging operation; and
deriving the amount of radiation to be emitted in the main imaging operation.

10. An image processing apparatus comprising at least one processor, the processor configured to:
acquire a radiographic image and imaging conditions in which the radiographic image has been captured; and
derive an amount of signal included in the radiographic image on the basis of the imaging conditions and a body thickness distribution of an object in the radiographic image and outputs a ratio of the derived amount of signal to an amount of noise included in the radiographic image as an index value of an amount of radiation emitted in the capture of the radiographic image; wherein
the processor acquires a radiographic image included in a series of radiographic images at a predetermined time during an imaging operation of capturing the series of radiographic images as a motion picture, and
the processor further performs control such that the emission of the radiation is stopped in the imaging operation in a case in which the index value is equal to or greater than a predetermined target value.

11. An image processing method comprising:
acquiring a radiographic image and imaging conditions in which the radiographic image has been captured;
deriving an amount of signal included in the radiographic image on the basis of the imaging conditions and a body thickness distribution of an object in the radiographic image;
outputting a ratio of the derived amount of signal to an amount of noise included in the radiographic image as an index value of an amount of radiation emitted in the capture of the radiographic image;
acquiring a radiographic image included in a series of radiographic images at a predetermined time during an imaging operation of capturing the series of radiographic images as a motion picture, and
performing control such that the emission of the radiation is stopped in the imaging operation in a case in which the index value is equal to or greater than a predetermined target value.

12. A non-transitory computer-readable storage medium that stores an image processing program that causes a computer to perform:
- acquiring a radiographic image and imaging conditions in which the radiographic image has been captured;
- deriving an amount of signal included in the radiographic image on the basis of the imaging conditions and a body thickness distribution of an object in the radiographic image;
- outputting a ratio of the derived amount of signal to an amount of noise included in the radiographic image as an index value of an amount of radiation emitted in the capture of the radiographic image;
- acquiring a radiographic image included in a series of radiographic images at a predetermined time during an imaging operation of capturing the series of radiographic images as a motion picture, and
- performing control such that the emission of the radiation is stopped in the imaging operation in a case in which the index value is equal to or greater than a predetermined target value.

\* \* \* \* \*